United States Patent [19]

Allain et al.

[11] 4,347,147

[45] * Aug. 31, 1982

[54] PROCESS FOR PREPARING OVERBASED MAGNESIUM SULFONATES

[75] Inventors: Ronald J. Allain, Naperville, Ill.; Dodd W. Fong, Richmond, Tex.

[73] Assignee: Nalco Chemical Company, Oak Brook, Ill.

[*] Notice: The portion of the term of this patent subsequent to Dec. 22, 1998, has been disclaimed.

[21] Appl. No.: 213,323

[22] Filed: Dec. 5, 1980

Related U.S. Application Data

[63] Continuation-in-part of Ser. No. 184,156, Sep. 4, 1980, Pat. No. 4,306,983, and a continuation-in-part of Ser. No. 24,230, Mar. 26, 1979, abandoned.

[51] Int. Cl.$^3$ .............................................. C10M 1/40
[52] U.S. Cl. ................................. 252/33.3; 252/18; 252/25; 252/33; 252/33.2; 252/33.4
[58] Field of Search ................... 252/18, 25, 33, 33.2, 252/33.3, 33.4

[56] References Cited

U.S. PATENT DOCUMENTS

| | | | |
|---|---|---|---|
| 3,223,630 | 12/1965 | Grayson | 252/18 X |
| 3,372,118 | 3/1968 | Rense | 252/33.4 X |
| 3,451,931 | 6/1969 | Kahn et al. | 252/25 X |
| 3,539,511 | 11/1970 | Sabol et al. | 252/33.4 X |
| 3,783,131 | 1/1974 | Le Suer | 252/25 X |
| 3,857,790 | 12/1974 | Saunders et al. | 252/18 X |
| 4,049,560 | 9/1977 | Dominey | 252/25 X |
| 4,059,536 | 1/1977 | Lallement et al. | 252/25 X |

*Primary Examiner*—Thomas A. Waltz
*Attorney, Agent, or Firm*—John G. Premo; Robert A. Miller

[57] ABSTRACT

A method of preparing superbased magnesium sulfonates by dispersing MgO in the preformed low viscosity overbased magnesium sulfonates. The low viscosity overbased magnesium sulfonates is prepared by sulfonating an alkyl benzene with a material containing $SO_3$, preferably oleum, and reacting the alkyl benzene sulfonate with magnesium oxide in the presence of a low viscosity diluent, such as No. 2 oil or LOPS (low odor paraffin solvent), together with water, alcohol, and $CO_2$. The newness of the method lies in the steps of preferably positively utilizing oleum which contains a minor amount of sulfuric acid as a promoter and utilizing also a surfactant couple of a $C_{12}$–$C_{18}$ fatty acid such as oleic acid and an ethanol amide such as a lauryl diethanol amide, which may be Witcamide 5138; where a ready made sulfonate is used, such as SA697 (Conoco), $H_2SO_4$ is utilized. In certain instances the amide may be omitted with satisfactory results occurring by using the acid alone.

Of particular interest is the preparation of a concentrated magnesium sulfonate wherein the water and alcohol are removed by distillation and a diluent such as LOPS or No. 2 oil is added to produce a slurry.

An important feature of this process lies in the reduction in size of the magnesium oxide particles. $CO_2$ is preferentially bubbled through the mixture after introduction of the magnesium oxide and at a temperature range of 30°–80° C. with stirring. A typical zone of particle size is 40–50% of about 200 A and 50–60% of 0.1–1.0 microns. This is quite advantageous where an emulsion is formulated and the percentage of magnesium is in the area of 14–23% and preferably 20% or over.

5 Claims, No Drawings

PROCESS FOR PREPARING OVERBASED MAGNESIUM SULFONATES

This application is a continuation-in-part of pending application Ser. No. 024,230 filed March 26, 1979, now abandoned and a continuation-in-part of Ser. No. 184,156, now U.S. Pat. No. 4,306,983.

This invention relates to a method of preparing superbased magnesium sulfonates by dispersing MgO in the preformed low viscosity overbased magnesium sulfonates. The low viscosity overbased magnesium sulfonates is preformed by sulfonating an alkyl benzene with a material containing $SO_3$, preferably oleum, and reacting the alkyl sulfonate with magnesium oxide in the presence of a low viscosity diluent, such as No. 2 oil or LOPS (low odor paraffin solvent), together with water, alcohol, and $CO_2$. The newness of the method lies in the steps of preferably positively utilizing oleum which contains a minor amount of sulfuric acid as a promoter or a ready made sulfonate with added sulfuric acid and utilizing also a surfactant couple of a $C_{12}$–$C_{18}$ fatty acid, such as oleic acid, and an ethanol amide, such as a lauryl diethanol amide, which is Witcamide 5138. Selected surfactants suitable for practicing this invention include the following, which are particular alkanol amides produced by Witco Chemical Corporation, New York: Witcamide 272, 511, 1017, 5130, 5133, 5140, 5145M, 5168, 5195, and AL69-8. In certain instances the amide may be omitted with satisfactory results occurring by using the acid alone.

Of particular interest is the preparation of a concentrated magnesium sulfonate wherein the water and alcohol are removed by distillation and a diluent, such as LOPS or No. 2 oil, is added to produce a slurry.

An important feature of this process lies in the reduction in size of the magnesium oxide particles. $CO_2$ is preferentially bubbled through the mixture after introduction of the magnesium oxide to the preformed overbased magnesium sulfonates and at a temperature range of 30°–80° C. with stirring.

In discussing size, the starting material of magnesium oxide, for example Martin Marietta's MM469, is in the range of 4–5 microns. This starting overbased magnesium sulfonates contain about 9–11% soluble magnesium salts which are colloidal materials of about 200 Å units. The remainder of the magnesium oxides added to make up a total of 20–25% magnesium after the initial formation of the magnesium sulfonate in the second step is less than 1 micron or in the range actually of about 0.1–1.0 micron. The percentage of magnesium is in the area of 14–23% and preferably 20% or over. The following percentiles are given from the examples noted post: Example 2, 11.9%; Example 3-A, 14.8%; Example 3-B, 15.2%; and Example 5, 22.7%.

The process comprises the following steps: (1) mixing the low-viscosity diluent oil with oil-soluble alkyl benzene sulfonic acid, water, alcohol, amine and an acid, and suspending agents together; (2) charging low density MgO into step (1); (3) treating the reaction mixture with $CO_2$ at 30°–80° C. with adequate stirring; (4) heating the final mixture to 120° C. to remove water and alcohol; and (5) charging more low density MgO into (4) with adequate stirring.

PRIOR ART STATEMENT

Of particular interest are the following U.S. Pat. Nos.: 2,695,910, 2,856,361, 3,429,811, 3,928,216, 4,129,589.

The patented art above is illustrative of many U.S. patents which have appeared in the past two decades on the present subject. In particular, in U.S. Pat. No. 3,928,216 Example 2 was used as a starting point for the present development. With reference to the recipe which is furnished in the examples and its components, the following is deemed of interest.

THE SULFONATING AGENT $SO_3$ gas or oleum have each been utilized in the past. In the event that a sulfonic acid is utilized, the following may be used: SA697 (Conoco), CHB (Witco Chemical, Dowfax 2AD (Dow Chemical). Additionally, when using alkyl benzenes, Exxon's ECA 5422 and Conoco's LMR-5 may be used. It is important to utilize sulfonic acids with a molecular weight in the range of 350–750 and especially between 400–600.

THE DILUENT OIL

The low boiling diluent oil used may well be selected from No. 2 fuel oil, for which see *Chemical Engineer's Handbook*, 5th edition, McGraw Hill, 1973, page 9-9, or LOPS (low odor paraffinic solvent), both of which have a low boiling point.

THE SURFACTANT COUPLE

The couple is defined to produce a surfactant which is a mixture of an acid and an amide. In order to accomplish this, a coupled arrangement of a fatty acid, such as oleic, is utilized, together with an alkanol amide.

THE CONCENTRATE

The product is a concentrate made by elimination of water and alcohol at up to 120° C. and replacement in part by low boiling solvents, addition of further magnesium oxide and $CO_2$ to produce a product of increased amount of magnesium which it was noted had a smaller particle size and thus was more susceptible to slurrying. The reduced particle size of the magnesium may have been due in part to the presence of the surfactant couple and other factors.

EXAMPLE 1-A

| | |
|---|---|
| LMR-5 SA (Conoco, sulfonated alkyl benzene, m.w. 385) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 2.5 grams |
| Water | 27.8 grams |
| Magnesium oxide (Martin Marietta 469) | 60.0 grams |

The above mix was heated at 35° C. with input of $CO_2$ at 0.96 liters/min. for one hour. The product had total base number (TBN) of 503. This was diluted with toluene and then was filtered to fill an extra need for a very pure product. This product had a TBN of 444.

EXAMPLE 1-B

| | |
|---|---|
| Conoco SA697 (low m.w. about 400 sulfonic acid) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grmms |
| Formic acid | 4.0 grams |
| Ethylene diamine (EDA) | 2.5 grams |
| Water | 27.8 grams |
| Magnesium oxide (Martin Marietta 469) | 60 grams |

The above mixture was heated at 45° C. with input of $CO_2$ at 0.96 liters/min. for one hour and solidified.

EXAMPLE 2

| | |
|---|---|
| A sulfonic acid from Exxon's ECA-5422 SA (alkyl benzene) | 52.0 grams |
| No. 2 fuel oil | 78.0 grams |
| Oleic acid | 10.0 grams |
| Witcamide 5138 (lauryl diethanol amide) | 5.0 grams |
| Methyl alcohol | 21.0 grams |
| Formic acid | 4.0 grams |
| Ethylene diamine (EDA) | 2.5 grams |
| Water | 27.8 grams |
| Magnesium oxide (Martin Marietta 469) | 70.0 grams |

The above recipe was warmed at 40° C. for one hour during which time $CO_2$ at 0.96 liters/min. was bubbled in. The temperature was then raised to greater than 100° C. to remove water and methyl alcohol. The product which was quite useful unfiltered had a TBN of 549 and for special purposes when filtered had a TBN of 419.

EXAMPLE 3A

| | |
|---|---|
| Exxon's ECA-5422 SA (alkyl benzene) sulfonated with $SO_3$ with 84% sulfonation | 46.8 grams |
| Concentrated sulfuric acid | 5.2 grams |
| No. 2 fuel oil | 78.0 grams |
| Oleic acid | 10.0 grams |
| Witcamide 5138 (lauryl diethanol amide) | 5.0 grams |
| Methyl alcohol | 27.3 grams |
| Formic acid | 4.0 grams |
| Ethylene diamine (EDA) | 2.5 grams |
| Water | 36.0 grams |
| Magnesium oxide (Martin Marietta 469) | 80.0 grams |

The recipe above was warmed from 48° C. to 65° C. together with bubbling $CO_2$ through at 0.96 liters/min. When the $CO_2$ sparging had ceased, the mixture was heated to about 115° C. for ½ hour to produce a viscous product with a TBN of 676, equivalent to 14.8% Mg.

EXAMPLE 3-B

| | |
|---|---|
| Alkyl benzene from Exxon's ECA 5422 sulfonated with $SO_3$ with 92% sulfonation | 46.8 grams |
| Remaining ingredients same as Example 3-A above. | |

This recipe is similar to Example 3-A and in the heating procedure the heating was carried out for one hour at 45° C. gradually warming to 53° C. and concomitant with $CO_2$ charging at 0.96 liters/min. When the $CO_2$ sparging stopped, heating was increased to 115° C. for an additional ½ hour and cooled. TBN of the product was 703, equivalent to 15.2% Mg.

EXAMPLE 4-A

| | |
|---|---|
| Part I | |
| Sulfonic acid | 47.6 grams |
| Concentrated sulfuric acid | 5.2 grams |
| LOPS | 78.0 grams |
| Methanol | 27.3 grams |
| Part II | |
| Formic acid | 4.0 grams |
| Ethylene diamine | 2.5 grams |
| Deionized water | 36.0 grams |

Part I and Part II were mixed together and to this was added magnesium oxide, 80 grams. Additionally, $CO_2$ was charged at 0.96 liter/min for one hour.

After one hour the water and methanol was stripped off by heating at about 120° C. The LOPS remained in the kettle having a boiling range of 188°–246° C. At this point 2.5 grams of toluene and 5 grams of Witcamide 5138 (lauryl diethanol amide) plus 10 grams of oleic acid were added to the pot with stirring. Finally, 60 grams of magnesium oxide was added with stirring for one hour.

EXAMPLE 4-B

A mixture of 75LOPS and 25% high boiling aromatic solvent were substituted for the LOPS in Example 1-A above. Additionally, the Witcamide was omitted and for the surfactant only oleic acid (10 grams) plus high boiling aromatic solvent (10 grams) were utilized.

EXAMPLE 5

| | |
|---|---|
| Sulfonated alkyl benzene | 47.6 grams |
| Concentrated $H_2SO_4$ | 5.2 grams |
| LOPS | 78.0 grams |
| Methyl alcohol | 27.3 grams |
| Formic acid (promoter) | 4.0 grams |
| Ethylene diamine (promoter) | 2.5 grams |
| Water | 36.0 grams |
| Magnesium oxide (Martin Marietta 469) | 80.0 grams |

The above mixture was warmed at 60° C. during which time $CO_2$ at 0.96 liters/min. was bubbled through for one hour and then heated to 115° C. Then the following was added:

| | |
|---|---|
| Witcamide 5138 (lauryl diethanol amide) | 5.0 grams |
| Oleic acid | 10.0 grams |
| Magnesium oxide (Martin Marietta 469) | 60.0 grams |
| Toluene | 100.0 grams |

The above was then stirred for 10 minutes, transferred to a flask, stripped of solvent. The TBN was 1052 or 22.7% magnesium by titration. The analysis by atomic absorption was as follows:

| | | | |
|---|---|---|---|
| Mg | 25% | | |
| K | 40 ppm | | |
| Na | 255 ppm | | |
| Ca | 1750 ppm | | |
| Na + K/Mg | = 40 + 255/250,000 | = 1/847 | |
| Ca/Mg | = 1750/250,000 | = 1/143 | |

EXAMPLE 6

| Mg sulfonates (Magox 98HR) | |
|---|---|
| Alkyl benzene sulfonic acid | 47.6 grams |
| Concentrated H$_2$SO$_4$ | 5.2 grams |
| LOPS | 78.0 grams |
| MeOH | 27.3 grams |
| Formic acid | 4.0 grams |
| Ethylene diamine | 2.5 grams |
| DI water | 36.0 grams |
| MgO (Magox 98HR) | 80.0 grams |

The above mixture was warmed from 40° C.–60° C. during which time CO$_2$ at 0.96 liters/min was bubbled through for one hour and then heated at 50°–120° C. Then the following was added with adequate stirring.

| Witcamide 5138 (lauryl diethanol amide) | 6.75 grams |
|---|---|
| Oleic acid | 13.5 grams |
| Toluene | 2.5 grams |
| MgO (Magox 98HR) | 60.0 grams |

TBN of the product was 1105, equivalent to 23.9% Mg.

EXAMPLE 7

| Mg sulfonates | |
|---|---|
| Alkyl benzene sulfonic acid | 47.6 grams |
| Concentrated H$_2$SO$_4$ | 5.2 grams |
| LOPS | 78.0 grams |
| MeOH | 27.3 grams |
| Formic acid | 4.0 grams |
| Ethylene diamine | 2.5 grams |
| DI water | 36.0 grams |
| MgO | 80.0 grams |

The above mixture was warmed from 40° C.–65° C. during which time CO$_2$ at 0.96 liters/min was bubbled through for one hour. Vacuum distilled, temperature went up to 125° C. Then the following was added:

| Toluene | 2.5 grams |
|---|---|
| Witcamide 5138 (lauryl diethanol amide) | 6.25 grams |
| Oleic acid | 12.5 grams |
| MgO | 60.0 grams |

The above mixture was stirred for 30 minutes. TBN of the product was 969, equivalent to 21% Mg.

EXAMPLE 8

| Mg sulfonate | | | |
|---|---|---|---|
| (1) | Alkyl benzene sulfonic acid | 286 grams | |
| | Concentrated sulfuric acid | 31.2 grams | |
| | LOPS or #2 fuel oil | 468 grams | |
| | Methanol | 164 grams | |
| (2) | Formic acid | 24 grams | |
| | Ethylene diamine | 15 grams | |
| | DI water | 216 grams | |
| (3) | MgO (Magox 98HR) | 480 grams | |
| (4) | CO$_2$ (Standard temperature and pressure) | 345 liters | |
| (5) | #2 fuel oil or Toluene | 15 grams | |
| | Witcamide 5138 (lauryl diethanol amide) | 30 grams | |
| | Oleic acid | 60 grams | |
| (6) | MgO (Magox 98HR) | 360 grams | |
| (7) | CO$_2$ (Standard temperature and pressure) | 172.8 liters | |
| (8) | MgO (Magox 98HR) | 0 to 120 g. or | |
| | #2 fuel oil | 0 to 30 g. | |
| A. | Stir 1 thoroughly; then add 2. | | |
| B. | Add 3 and allow to be thoroughly mixed. Keep temperature below 60° C. to minimize solvent loss. | | |
| C. | Charge CO$_2$ at 5.76 l/min for one hour at low reflux. Temperature should be below 60° C. | | |
| D. | After CO$_2$ charge, add 5. Stir for 3 min. | | |
| E. | Add 6 with stirring. | | |
| F. | Charge CO$_2$ at 5.76 l/min for ½ hour. | | |
| G. | Distill solvents at temperature below 80° C. about 200 mm Hg. | | |
| H. | Check Brookfield viscosity. Add either MgO or #2 fuel oil to adjust final product viscosity to 5000–6000 cps at room temperature. | | |

We claim:

1. In the method of preparing overbased magnesium sulfonates by sulfonating an alkyl benzene with a material containing SO$_3$ which material is selected from one member of the group consisting of SO$_3$ and oleum and reacting the alkyl sulfonate product with magnesium oxide in the presence of a low viscosity diluent, water, alcohol, and CO$_2$, the improvement which comprises positively utilizing oleum in the sulfonation step and additionally adding to the original overbased magnesium sulfonate sufficient magnesium oxide and a surfactant couple comprising a C$_{12}$–C$_{18}$ fatty acid and an alkanol amide which produces a superbased magnesium sulfonate with a magnesium content of about 14–23% and a zone particle size of about 40% 200 Å and about 60% 0.1–1.0 microns.

2. The method of claim 1 wherein an alkyl benzene sulfonic acid with added sulfuric acid is utilized instead of the alkyl benzene sulfonic acid.

3. The method according to claim 1 which consists of using as the surfactant couple oleic acid and lauryl diethanol amide.

4. The method according to claim 1 wherein carbon dioxide is additionally bubbled through the slurry at 30°–80° C. with stirring.

5. A superbased magnesium oxide derived from overbased magnesium sulfonates incorporated in a slurry, prepared by the method of claim 1 and which comprises a magnesium oxide at a viscosity of about 5,000 centipoise and a particle size of about 40% 200 Å and about 60% 0.1–1.0 microns.

* * * * *